United States Patent
Sowa et al.

(10) Patent No.: US 8,324,233 B2
(45) Date of Patent: Dec. 4, 2012

(54) CO-CRYSTALS OF PYRIMETHANIL AND DITHIANON

(75) Inventors: Christian Sowa, Neustadt (DE); Heidi Emilia Saxell, Carlsberg (DE); Ralf Vogel, Limburgerhof (DE)

(73) Assignee: BASF SE, Lugwigshafen (DE)

( * ) Notice: Subject to any disclaimer, the term of this patent is extended or adjusted under 35 U.S.C. 154(b) by 457 days.

(21) Appl. No.: 12/676,267

(22) PCT Filed: Aug. 22, 2008

(86) PCT No.: PCT/EP2008/061000
§ 371 (c)(1),
(2), (4) Date: Mar. 3, 2010

(87) PCT Pub. No.: WO2009/047043
PCT Pub. Date: Apr. 16, 2009

(65) Prior Publication Data
US 2010/0184792 A1    Jul. 22, 2010

(30) Foreign Application Priority Data

Sep. 7, 2007  (EP) .................................. 07115950

(51) Int. Cl.
*A01N 43/54* (2006.01)
*C07D 239/42* (2006.01)

(52) U.S. Cl. ...................................... 514/275; 544/330

(58) Field of Classification Search .................. 514/275; 544/330
See application file for complete search history.

(56) References Cited

FOREIGN PATENT DOCUMENTS

| DE | 151 404 | 10/1981 |
|---|---|---|
| GB | 857 383 | 12/1960 |
| WO | WO 2004/004461 | 1/2004 |

OTHER PUBLICATIONS

International Search Report for International Application No. PCT/EP2008/061000; International Filing Date: Aug. 22, 2008.
International Preliminary Report on Patentability for International Application No. PCT/EP2008/061000; International Filing Date: Aug. 22, 2008.

*Primary Examiner* — Kristin Bianchi
(74) *Attorney, Agent, or Firm* — Brinks Hofer Gilson & Lione

(57) ABSTRACT

The present invention relates to co-crystals of pyrimethanil and dithianon, which, in a X-ray powder diffractogram at 25° C. show at least three of the following reflexes:

$2\theta=7.46\pm0.20$
$2\theta=9.98\pm0.20$
$2\theta=13.28\pm0.20$
$2\theta=23.09\pm0.20$
$2\theta=24.38\pm0.20$
$2\theta=27.01\pm0.20$ a process for their preparation and their use for the preparation of compositions for crop protection.

20 Claims, 2 Drawing Sheets

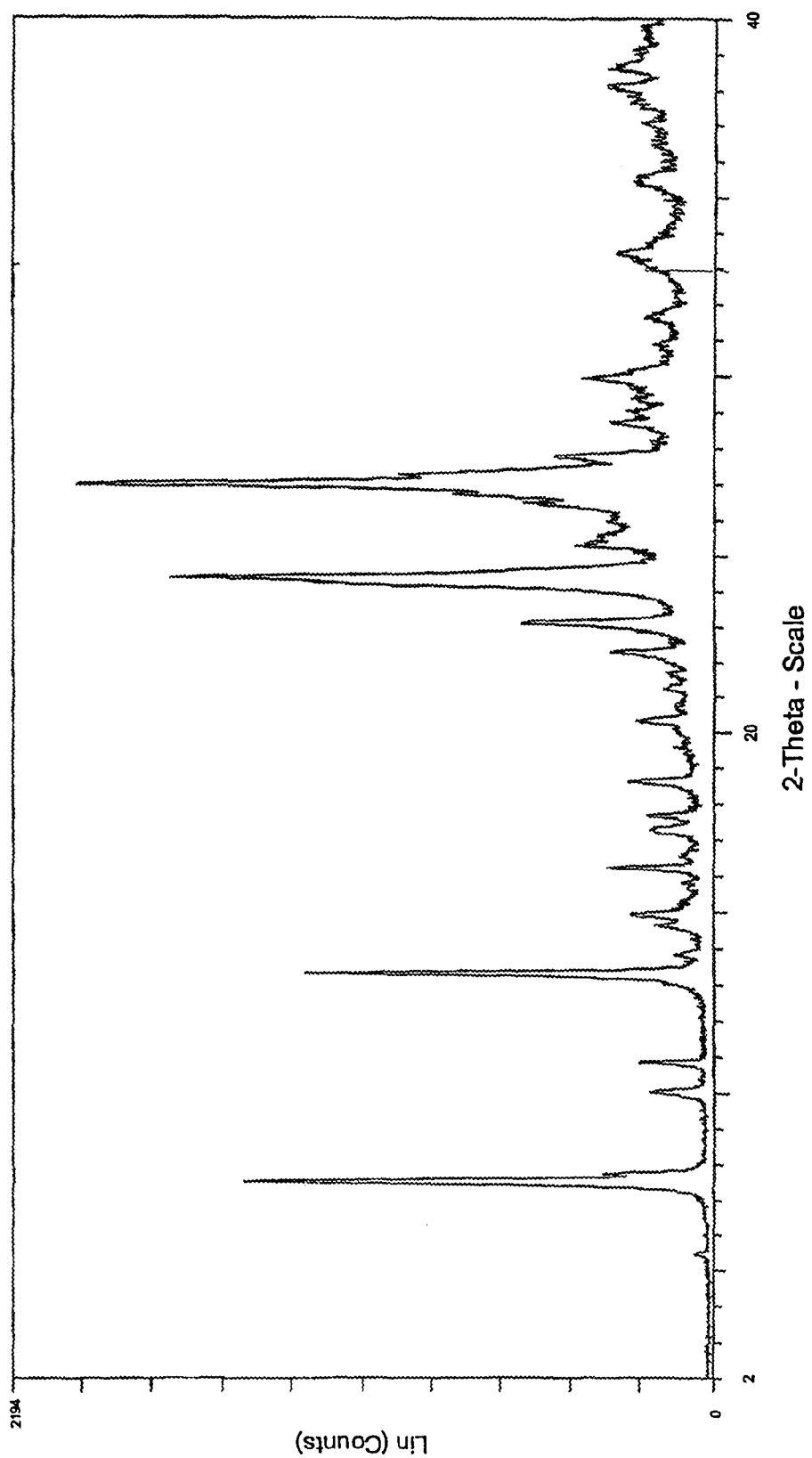
Figure 1. Powder diffraction pattern of co-crystals of pyrimethanil and dithianon

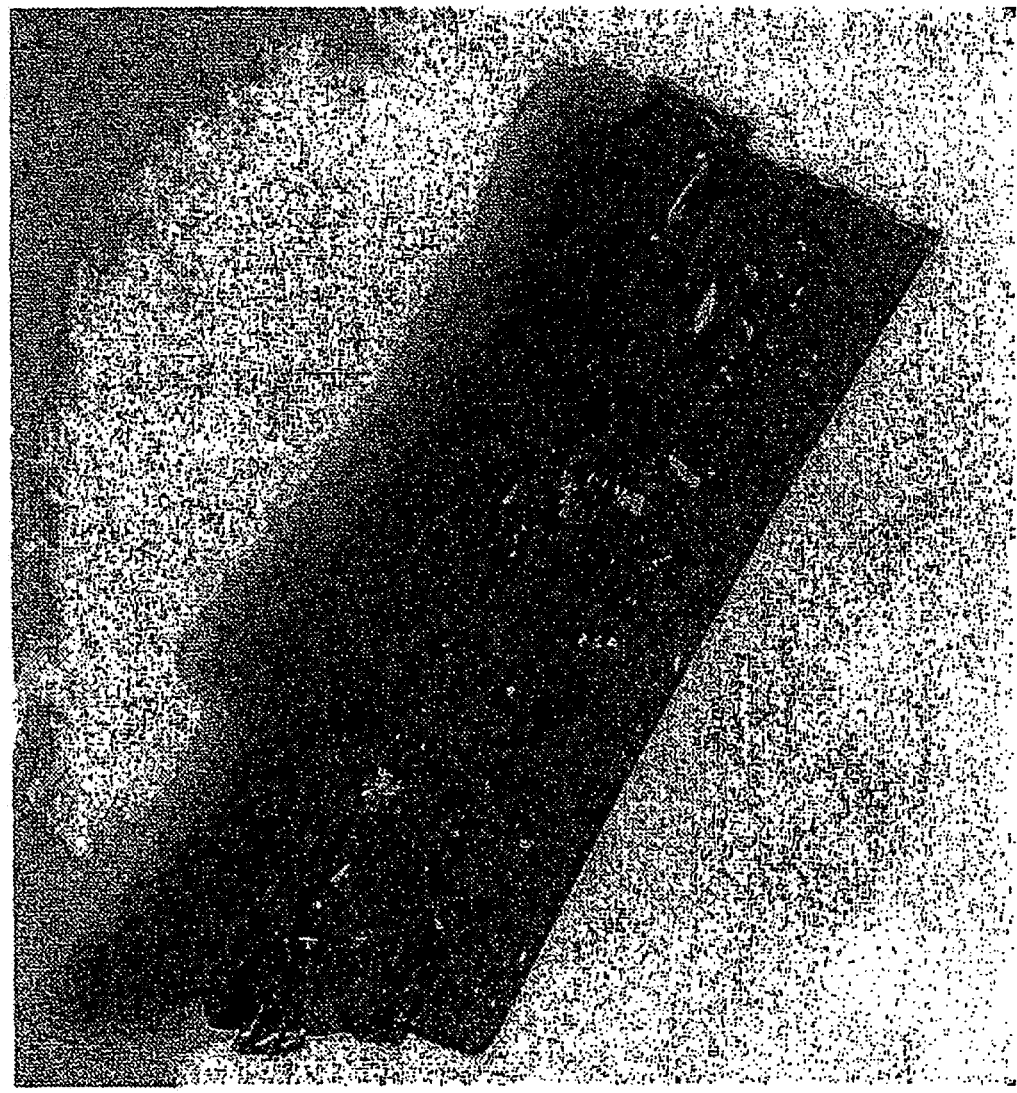
Figure 2. Light microscop picture of a co-crystal of pyrimethanil and dithianon

CO-CRYSTALS OF PYRIMETHANIL AND DITHIANON

This application is a National Stage application of International Application No. PCT/EP2008/061000 filed Aug. 22, 2008, the entire contents of which is hereby incorporated herein by reference. This application also claims the benefit under 35 U.S.C. §119 of European Patent Application No. 07115950.3, filed Sep. 7, 2007, the entire contents of which is hereby incorporated herein by reference.

The present invention relates to novel co-crystals of pyrimethanil and dithianon, to processes of their preparation and to the use of the novel co-crystals for the preparation of compositions for crop protection.

Pyrimethanil is known as a fungicide and described in DD-A 151 404.

Dithianon is known as a fungicide and described in GB-A 857 383.

WO 2004/004461 describes mixtures of pyrimethanil and dithianon which are synergistic. All biological experiments were conducted in a solution of the mixture in aceton and DMSO. After adding 1% of an emulgator the solution was mixed with water to the desired concentration. Suspension concentrates were not described in this document.

During the preparation of a suspension concentrate (SC) of pyrimethanil and dithianon, the concentrate changed the colour from brown to dark green/black and the concentrate solidified and could not be used for the preparation of crop protection formulations.

Accordingly, it was an object of the present invention to provide a mixture of pyrimethanil and dithianon in a form which permits the preparation of suspension concentrates which are flowable and stable.

This object has been achieved by the co-crystals of pyrimethanil and dithianon as described below.

Thus, the present invention relates to co-crystals of pyrimethanil and dithianon, which, in a X-ray powder diffractogram at 25° C., show at least three, in particular at least 4 and preferably all of the following 2θ values [°]:

2θ=7.46±0.20

2θ=9.98±0.20

2θ=13.28±0.20

2θ=23.09±0.20

2θ=24.38±0.20

2θ=27.01±0.20

A single crystal structure analysis of the dark green or black coloured single crystals of the crystalline complex of dithianone and pyrimethanil, reveals a monoclinic crystal system and space group P2(1)/n. The important unit cell parameters measured at −170° C. can be seen in table 1. The ratio of dithianone and pyrimethanil in this co-crystalline is a 1:1. The complex between dithianone and pyrimethanil is formed via strong hydrogen bonding in between the NH-group of pyrimethanil and one of the carbonyle groups of dithianone (N—H . . . O angle 168.1°).

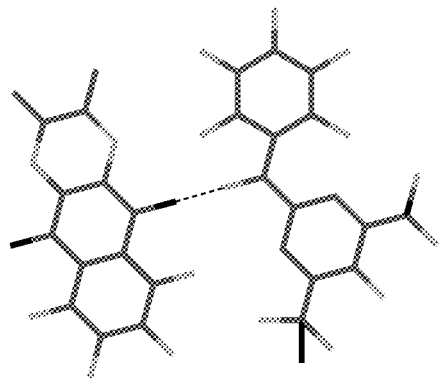

FIG. 1: Single crystal structure of dithianon and pyrimethanile co-crystal.

TABLE 1

Crystallographic data of the crystalline complex of dithianone and pyrimethanil at −170° C.

| Parameter | |
|---|---|
| Class | Monoclinic |
| Space group | P-1 |
| a | 717.0(1) pm |
| b | 2278.5(2) pm |
| c | 1381.3(2) pm |
| α | 90° |
| β | 97.069(5)° |
| γ | 90° |
| Volume | 2.2395(4) nm$^3$ |
| Z | 4 |
| Density (calculated) | 1.470 g/cm$^3$ |
| R1, wR2 | 0.039, 0.097 | a, b, c = Length of the edges of the unit cell
α, β, γ = Angles of the unit cell
Z = Number of dithianon and pyrimethanil compelexes (1:1) in the unit cell For example, the crystalline complex of dithianone and pyrimethanil shows in an X-ray powder diffractogram at 25° C. (Cu—Kα-radiation, 1,54178 Å) at least 3, in particular at least 4, and preferably at least 8 and more preferably all of the following reflexes, given in the following table 3 as 2θ values or as lattice spacings d.

TABLE 3

PXRD of the co-crystals of pyrimethanil and dithianon

| 2θ values [°] | d [nm] |
|---|---|
| 7.46 ± 0.20 | 11.86 ± 0.3 |
| 9.98 ± 0.20 | 8.87 ± 0.2 |
| 13.28 ± 0.20 | 6.67 ± 0.1 |
| 14.90 ± 0.20 | 5.95 ± 0.06 |
| 18.6 ± 0.20 | 4.77 ± 0.05 |
| 20.30 ± 0.20 | 4.38 ± 0.03 |
| 23.09 ± 0.20 | 3.85 ± 0.03 |
| 24.38 ± 0.20 | 3.65 ± 0.02 |
| 27.01 ± 0.20 | 3.30 ± 0.02 |
| 29.94 ± 0.20 | 2.99 ± 0.02 |

From a TGA/DTA measurement, confirmed with a hot stage microscopy measurement, it can be stated that the melting point is in between 165 and 175° C., in particular in between 166 and 173° C.

In the co-crystal according to said embodiment of the present invention, the molar ratio of pyrimethanil and dithianone is from 2:1 to 1:2 and in particular about 1:1.

The crystalline complex of the present invention can be prepared by co-crystallizing dithianone and pyrimethanil from a solution or slurry or from a melt containing both components. The ratio of the compounds is not critical as the 1:1 co-crystal will form leaving the excess of the other components intact. Likewise, it is possible to prepare the crystalline complexes of the present invention, by mixing or grinding a mixture of dithianone and pyrimethanil as dry compounds, in aqueous or vegetable or mineral oil based media.

The co-crystals of the present invention are suitable for the preparation of compositions for crop protection, in particular for the preparation of aqueous suspension concentrates.

Accordingly, the invention also provides a composition for crop protection, comprising co-crystals of pyrimethanil and dithianon and carriers and/or auxiliaries.

Suitable carriers are, in principle, all solid substances usually used in crop protection compositions, in particular in fungicides. Solid carriers are, for example, mineral earths, such as silica gels, silicates, talc, kaolin, attaclay, limestone, lime, chalk, bole, loess, clay, dolomite, diatomaceous earth, calcium sulfate and magnesium sulfate, magnesium oxide, ground synthetic materials, fertilizers, such as, for example, ammonium sulfate, ammonium phosphate, ammonium nitrate, ureas and products of vegetable origin, such as cereal meal, tree bark meal, wood meal and nutshell meal, cellulose powders and other solid carriers.

Suitable liquid carriers are, in principle, water and also organic solvents in which the co-crystals have low or no solubility, for example those in which the solubility of the co-crystals at 25° C. and 1013 mbar is not more than 1% by weight, in particular not more than 0.1% by weight and especially not more than 0.01% by weight. Examples for liquid carriers include water, vegetable oils, such as soybean oil, corn oil, sunflower oil, olive oil, esters of fatty acids such as methyloleate or mineral oils such as light petroleum oil, Bayol 85, Exxsol D 130, Exxsol D 140, the Isopar product range from Exxon Chemicals.

Typical auxiliaries comprise surfactants, in particular the wetting agents and dispersants usually employed in crop protection compositions, furthermore viscosity-modifying additives (thickeners), antifoam agents, antifreeze agents, agents for adjusting the pH, stabilizers, anticaking agents and biocides (preservatives).

The invention relates in particular to compositions for crop protection in the form of an aqueous suspension concentrate (SC). Such suspension concentrates comprise the co-crystals in a finely divided particulate form, where the particles of the co-crystals are suspended in an aqueous medium. The size of the particles of the co-crystals, i.e. the size which is not exceeded by 90% by weight of the active compound particles, is typically below 30 µm, in particular below 20 µm. Advantageously, at least 40% by weight and in particular at least 60% by weight of the particles in the SCs according to the invention have diameters below 2 µm.

In addition to the co-crystals, suspension concentrates typically comprise surfactants, and also, if appropriate, antifoam agents, thickeners, antifreeze agents, stabilizers (biocides), agents for adjusting the pH and anticaking agents.

In such SCs, the amount of the co-crystals and, if appropriate, further active compounds is usually in the range from 10 to 70% by weight, in particular in the range from 20 to 50% by weight, based on the total weight of the suspension concentrate.

Preferred surfactants are anionic and nonionic surfactants. Suitable surfactants also include protective colloids. The amount of surfactants will generally be from 0.5 to 20% by weight, in particular from 1 to 15% by weight and particularly preferably from 1 to 10% by weight, based on the total weight of the SCs according to the invention. Preferably, the surfactants comprise at least one anionic surfactant and at least one non-ionic surfactant, the ratio of anionic to nonionic surfactant typically being in the range from 10:1 to 1:10.

Examples of anionic surface-active substances (surfactants) include alkylaryl sulfonates, phenyl sulfonates, alkyl sulfates, alkyl sulfonates, alkyl ether sulfates, alkylaryl ether sulfates, alkyl polyglycol ether phosphates, polyaryl phenyl ether phosphates, alkyl sulfosuccinates, olefin sulfonates, paraffin sulfonates, petroleum sulfonates, taurides, sarcosides, fatty acids, alkylnaphthalenesulfonic acids, naphthalenesulfonic acids, lignosulfonic acids, condensates of sulfonated naphthalenes with formaldehyde or with formaldehyde and phenol and, if appropriate, urea, and also condensates of phenolsulfonic acid, formaldehyde and urea, lignosulfite waste liquors and lignosulfonates, alkyl phosphates, alkylaryl phosphates, for example tristyryl phosphates, and also polycarboxylates, such as, for example, polyacrylates, maleic anhydride/olefin copolymers (for example Sokalan® CP9, BASF), including the alkali metal, alkaline earth metal, ammonium and amine salts of the substances mentioned above. Preferred anionic surfactants are those which carry at least one sulfonate group, and in particular their alkali metal and their ammonium salts.

Examples of nonionic surfactants comprise alkylphenol alkoxylates, tristyrylphenol alkoxylates (e.g. Soprophor BSU), alcohol alkoxylates, fatty amine alkoxylates, polyoxyethylene glycerol fatty acid esters, castor oil alkoxylates, fatty acid alkoxylates, fatty amide alkoxylates, fatty polydiethanolamides, lanolin ethoxylates, fatty acid polyglycol esters, isotridecyl alcohol, fatty amides, methylcellulose, fatty acid esters, alkyl polyglycosides, glycerol fatty acid esters, polyethylene glycol, polypropylene glycol, polyethylene glycol/polypropylene glycol block copolymers (e.g. Pluoronic PE 10500), polyethylene glycol alkyl ethers, polypropylene glycol alkyl ethers, polyethylene glycol/polypropylene glycol ether block copolymers (polyethylene oxide/polypropylene oxide block copolymers) and mixtures thereof. Preferred nonionic surfactants are fatty alcohol ethoxylates, alkyl polyglycosides, glycerol fatty acid esters, castor oil alkoxylates, fatty acid alkoxylates, fatty amide alkoxylates, lanolin ethoxylates, fatty acid polyglycol esters and ethylene oxide/propylene oxide block copolymers and mixtures thereof.

Typical protective colloids are water-soluble amphiphilic polymers. Examples of these are proteins and denatured proteins, such as casein, polysaccharides, such as water-soluble starch derivatives and cellulose derivatives, in particular hydrophobically modified starches and celluloses, furthermore polycarboxylates, such as polyacrylic acid and acrylic acid copolymers, polyvinyl alcohol, polyvinylpyrrolidone, vinylpyrrolidone copolymers, polyvinylamines, polyethyleneimines and polyalkylene ethers.

In particular, the SCs according to the invention comprise at least one surfactant which improves wetting of the plant parts by the aqueous application form (wetting agent) and at least one surfactant which stabilizes the dispersion of the active compound particles in the SC (dispersant). The amount of wetting agent is typically in the range from 0.5 to 10% by weight, in particular from 0.5 to 5% by weight and especially from 0.5 to 3% by weight, based on the total weight of the SC. The amount of dispersant is typically from 0.5 to 10% by weight and in particular from 0.5 to 5% by weight, based on the total weight of the SC.

Preferred wetting agents are of anionic or nonionic nature and selected, for example, from naphthalenesulfonic acids including their alkali metal, alkaline earth metal, ammonium and amine salts, furthermore fatty alcohol ethoxylates, fatty alcohol alkoxylates (e.g. Atplus 245), alkali metal sulfosuccinates (e.g. Lutensit A-BO) alkyl polyglycosides, glycerol fatty acid esters, castor oil alkoxylates, fatty acid alkoxylates, fatty amide alkoxylates, fatty polydiethanolamides, lanolin ethoxylates and fatty acid polyglycol esters.

Preferred dispersants are of anionic or nonionic nature and selected, for example, from polyethylene glycol/polypropylene glycol block copolymers (e.g. Pluronic PE 10500), polyethylene glycol alkyl ethers, polypropylene glycol alkyl ethers, polyethylene glycol/polypropylene glycol ether block copolymers, alkylaryl phosphates, for example tristyryl phosphates, lignosulfonic acids (e.g. Reax 910), condensates of sulfonated naphthalenes (e.g. Morwet 3 D 425) with formaldehyde or with formaldehyde and phenol and, if appropriate, urea, and also condensates of phenolsulfonic acid, formaldehyde and urea, lignosulfite waste liquors and lignosulfonates, polycarboxylates, such as, for example, polyacrylates, maleic anhydride/olefin copolymers (for example Sokalan® CP9, BASF), including the alkali metal, alkaline earth metal, ammonium and amine salts of the substances mentioned above.

Viscosity-modifying additives (thickeners) suitable for the SCs according to the invention are in particular compounds which bestow upon the formulation pseudoplastic flow properties, i.e. high viscosity in the resting state and low viscosity in the agitated state. Suitable are, in principle, all compounds used for this purpose in suspension concentrates. Mention may be made, for example, of inorganic substances, such as bentonites or attapulgites (for example Attaclay® from Engelhardt), and organic substances, such as polysaccharides and heteropolysaccharides, such as Xanthan Gum® (Kelzan® from Kelco), Rhodopol® 23 (Rhone Poulenc) or Veegum® (from R.T. Vanderbilt), and preference is given to using Xanthan-Gum®. Frequently, the amount of viscosity-modifying additives is from 0.1 to 5% by weight, based on the total weight of the SC.

Antifoam agents suitable for the SCs according to the invention are, for example, silicone emulsions known for this purpose (Silikon® SRE, from Wacker, or Rhodorsil® from Rhodia), long-chain alcohols, fatty acids, defoamers of the type of aqueous wax dispersions, solid defoamers (so-called Compounds), organofluorine compounds and mixtures thereof. The amount of antifoam agent is typically from 0.1 to 1% by weight, based on the total weight of the SC.

Preservatives may also be added for stabilizing the suspension concentrates according to the invention. Suitable preservatives are those based on isothiazolones, for example Proxel® from ICI or Acticide® RS or Acticide® MBS from Thor Chemie or Kathon® MK from Rohm & Haas. The amount of preservatives is typically from 0.05 to 0.5% by weight, based on the total weight of the SC.

Suitable antifreeze agents are liquid polyols, for example urea, ethylene glycol, propylene glycol or glycerol. The amount of antifreeze agents is generally from 1 to 20% by weight, in particular from 5 to 10% by weight, based on the total weight of the suspension concentrate.

If appropriate, the SCs according to the invention may comprise buffers for regulating the pH. Examples of buffers are alkali metal salts of weak inorganic or organic acids, such as, for example, phosphoric acid, boric acid, acetic acid, propionic acid, citric acid, fumaric acid, tartaric acid, oxalic acid and succinic acid.

Suitable colorants are all dyes and pigments customary for such purposes. Both sparingly water-soluble pigments and water-soluble dyes can be used. Examples which may be mentioned are the dyes and pigments known under the names Rhodamine B, C.I. Pigment Red 112 and C.I. Solvent Red 1, Pigment blue 15:4, Pigment blue 15:3, Pigment blue 15:2, Pigment blue 15:1, Pigment blue 80, Pigment yellow 1, Pigment yellow 13, Pigment red 48:2, Pigment red 48:1, Pigment red 57:1, Pigment red 53:1, Pigment orange 43, Pigment orange 34, Pigment orange 5, Pigment green 36, Pigment green 7, Pigment white 6, Pigment brown 25, Basic violet 10, Basic violet 49, Acid red 51, Acid red 52, Acid red 14, Acid blue 9, Acid yellow 23, Basic red 10, Basic red 108. The amount of colorant is usually not more than 20% by weight of the formulation and preferably in the range of from 0.1 to 15% by weight, based on the total weight of the formulation.

Suitable tackifiers are all binders customarily used in seed dressings. Examples of suitable binders include thermoplastic polymers, such as polyvinylpyrrolidone, polyvinyl acetate, polyvinyl alcohol and tylose, furthermore polyacrylates, polymethacrylates, polybutenes, polyisobutenes, polystyrene, polyethyleneamine, polyethyleneamide, the protective colloids mentioned above, polyesters, polyether esters, polyanhydrides, polyester urethanes, polyester amides, thermoplastic polysaccharides, for example cellulose derivatives, such as cellulose esters, cellulose ethers, cellulose ether esters, including methylcellulose, ethylcellulose, hydroxymethylcellulose, carboxymethylcellulose, hydroxypropylcellulose and starch derivatives and modified starches, dextrins, maltodextrins, alginates and chitosans, furthermore fats, oils, proteins, including casein, gelatine and zein, gum Arabic, shellac. The tackifiers are preferably compatible with plants, i.e. they have no significant, if any, phytotoxic action. The tackifiers are preferably biodegradable. Preferably, the tackifier is chosen such that it acts as a matrix for the active components of the formulation. The amount of tackifier is usually not more than 40% by weight of the formulation and preferably in the range of from 1 to 40% by weight and in particular in the range of from 5 to 30% by weight, based on the total weight of the formulation.

In addition to the tackifier, the formulation may also comprise inert fillers. Examples of these are the solid carrier materials mentioned above, in particular finely divided inorganic materials, such as clays, chalk, bentonite, kaolin, talc, perlite, mica, silica gel, diatomaceous earth, quartz powder, montmorillonite, and also finely divided organic materials, such as wood meal, cereal meal, activated carbon and the like. The amount of filler is preferably chosen such that the total amount of filler does not exceed 75% by weight, based on the total weight of all non-volatile components of the formulation. Frequently, the amount of filler is in the range of from 1 to 50% by weight, based on the total weight of all non-volatile components of the formulation.

In addition, the formulation may also comprise a plasticizer which increases the flexibility of the coating. Examples of plasticizers are oligomeric polyalkylene glycols, glycerol, dialkyl phthalates, alkyl benzyl phthalates, glycol benzoates and similar compounds. The amount of plasticizer in the coating is frequently in the range of from 0.1 to 20% by weight, based on the total weight of all non-volatile components of the formulation.

Suitable preparation methods for the co-crystals of pyrimethanil and dithianon are as follows.

As stated above, for the preparation of the co-crystals equimolar amounts of pyrimethanil and dithianon are dissolved in polar solvents such as DMSO, acetronitril, DMF or aceton at room temperature under agitation. The solvent is evaporated to yield the co-crystals of pyrimthanil and dithianon.

In another process for the preparation of the co-crystals equimolar amounts of pyrimethanil and dithianon are thoroughly mixed and dry grinded, optionally at elevated temperatures.

In a further process for the preparation of the co-crystals equimolar amounts of pyrimethanil and dithianon were thoroughly mixed with a liquid carrier such as water, vegetable or mineral based oil followed by grinding, optionally at elevated temperatures.

Preparation Method I for the Preparation of a Stable Composition of Co-Crystals of Pyrimethanil and Dithianon:

Two separate premixes were prepared by thoroughly mixing water, dispersants, emulsifier, antifreeze, wetting agents, antifoam and/or bactericides and pyrimethanil or dithianon, respectively at room temperature, optionally at elevated temperatures.

The two premixes, which are not ground suspensions, are mixed together in one beaker under stirring at 20 to 100° C., preferably at 20 to 70° C., most preferred at about 50° C. After one hour, the suspension has changed from brown colour to dark green. The suspension is cooled to 20° C. and then milled over a glass-bead mill to obtain a particle size distribution (PSD) 80%<2 μm. The product has a viscosity of less than 50 mPas. The viscosity might be further adjusted by addition of thickeners like xanthan gum. Further additives that might be added at this stage include, but are not restricted to biocides, antifoam and further rheology modifiers. The product stays unchanged at room temperature for at least 4 months. The particle size distribution is very stable during this time.

Preparation method II: The premix containing both, pyrimethanil and dithianon, is passed continuously over a bead-mill at elevated temperature. After half an hour, the complete suspension has turned dark green. The mill is cooled to 20° C. and milling is extended until a PSD of 80%<2 μm is achieved. The viscosity might be further adjusted by addition of thickeners like xanthan gum. Further additives that might be added at this stage include, but are not restricted to biocides, antifoam and further rheology modifiers.

Preparation method III: A premix is prepared by thoroughly mixing pyrimethanil, water and dispersants and further formulation additives. To this suspension premix is added the calculated amount of dithianon under agitation. After all dithianon has been added, the mixture is heated to 50° C. for 1 hour. The suspension has turned dark green and after cooling it down to 20° C. it is being milled over a bead mill to obtain a PSD of 80%<2 μm. The viscosity might be further adjusted by addition of thickeners like xanthan gum. Further additives that might be added at this stage include, but are not restricted to biocides, antifoam and further rheology modifiers.

Preparation method IV: A premix is prepared by thoroughly mixing dithianon, water and dispersants and further formulation additives. To this suspension premix is added the calculated amount of pyrimethanil under agitation. After all pyrimethanil has been added, the mixture is heated to 50° C. for 1 hour. The suspension has turned dark green and after cooling it down to 20° C. it is being milled over a bead mill to obtain a PSD of 80%<2 μm. The viscosity might be further adjusted by addition of thickeners like xanthan gum. Further additives that might be added at this stage include, but are not restricted to biocides, antifoam and further rheology modifiers.

Preparation method V: Dithianon and pyrimethanil are suspended together with suitable dispersants and emulsifiers in a mineral or vegetable based oil, such as white oil, Bayol 85, sun flower oil, rape seed oil, corn oil and methyloleate. The OD (oil dispersion) premix is heated under stirring to 50° C. until the colour of the suspension has turned from brown to dark green (1 hour). Then the premix is cooled down and grinded over a bead mill to obtain a PSD of 80%<2 μm. The viscosity might be further adjusted by addition of thickeners like xanthan gum. Further additives that might be added at this stage include, but are not restricted to biocides, antifoam and further rheology modifiers.

Preparation method VI: Solutions of dithianon and pyrimethanil in polar solvents like DMSO, Acetonitril, DMF or aceton are prepared under mixing. The solvent is evaporated to yield the co-crystals. These are suspended in water and formulation additives (same as for suspension concentrate) and first pre-ground over a PUC mill and then finely ground over a bead mill to achieve a PSD of 80%<2 μm. The viscosity might be further adjusted by addition of thickeners like xanthan gum. Further additives that might be added at this stage include, but are not restricted to biocides, antifoam and further rheology modifiers.

Preparation method VII: Dry dithianon and pyrimethanil are thoroughly mixed and kept at 50° C. under agitation. After some hours, the powdery product has turned its colour to olive green. To the cooled co-crystal premix, dispersants, antifoams, wetting agents, adjuvants and fillers are added as typical for WG, WP and WDG formulations. Then the premix is processed either by extrusion to give a WDG (water dispersible granule) formulation or it is used after a finishing step as WP (wettable powder). It may also be suspended in water and then spray dried to give a water dispersible granule.

Preparation method VIII: A suspension premix of pyrimethanil and dithianon is being prepared as described in example no. III. This premix is then run over a bead mill to give a PSD of 80%<2 μm. The resulting suspension is then spray dried to give a WDG formulation.

The weight ratio of pyrimethanil to dithianon in the compositions is from 100:1 to 1:100, preferably from 20:1 to 1:20, in particular from 10:1 to 1:10 and most preferred 2:3.

The co-crystals of pyrimethanil and dithianon are distinguished by an invigorating and yield-increasing effect on plants, in particular leguminous plants, and excellent efficacy against a broad spectrum of phytopathogenic fungi, in particular from the classes of the Ascomycetes, Deuteromycetes, Basidiomycetes and Peronosporomycetes (syn. Oomycetes). They are systemically effective and can be employed in crop protection as foliar fungicides, as fungicides for seed dressing and as soil fungicides.

They are of particular importance for the control of a large number of fungi on various crop plants such as bananas, cotton, vegetable species (for example cucumbers, beans and cucurbits), barley, grass, oats, coffee, potatoes, corn, fruit plants, rice, rye, soybeans, tomatoes, grapevines, wheat, ornamental plants, sugar cane and a large number of seeds.

They are advantageously suitable for controlling the following plant diseases:

*Alternaria* species on vegetable species, oilseed rape, sugar beet and fruit and rice, such as, for example,

*A. solani* or *A. alternata* on potatoes and tomatoes,

*Aphanomyces* species on sugar beet and vegetable species,

*Ascochyta* species on cereals and vegetable species,

*Bipolaris* and *Drechslera* species on corn, cereals, rice and lawn, such as, for example, *D. maydis* on corn,
*Blumeria graminis* (powdery mildew) on cereals,
*Botrytis cinerea* (gray mold) on strawberries, vegetable species, flowers and grapevines,
*Bremia lactucae* on lettuce,
*Cercospora* species on corn, soybeans, rice and sugar beet,
*Cochliobolus* species on corn, cereals, rice, such as, for example, *Cochliobolus sativus* on cereals, *Cochliobolus miyabeanus* on rice,
*Colletotricum* species on soybeans and cotton,
*Drechslera* species, *Pyrenophora* species on corn, cereals, rice and lawn, such as, for example, *D. teres* on barley or *D. tritici-repentis* on wheat,
Esca on grapevines, caused by *Phaeoacremonium chiamydosporium*, *Ph. Aleophilum*, and *Formitipora punctata* (syn. *Phellinus punctatus*),
*Elsinoe ampelina* on grapevines,
*Exserohilum* species on corn,
*Erysiphe cichoracearum* and *Sphaerotheca fuliginea* on cucumber species,
*Fusarium* and *Verticillium* species on various plants, such as, for example, *F. graminearum* or *F. culmorum* on cereals or *F. oxysporum* on a large number of plants, such as, for example, tomatoes,
*Gaeumanomyces graminis* on cereals,
*Gibberella* species on cereals and rice (for example *Gibberella fujikuroi* on rice),
*Glomerella cingulata* on grapevines and other plants,
Grainstaining complex on rice,
*Guignardia budwelli* on grapevines,
*Helminthosporium* species on corn and rice,
*Isariopsis clavispora* on grapevines,
*Michrodochium nivale* on cereals,
*Mycosphaerella* species on cereals, bananas and peanuts, such as, for example, *M. graminicola* on wheat or *M. fijiensis* on bananas,
*Peronospora* species on cabbage and bulbous plants, such as, for example, *P. brassicae* on cabbage or *P. destructor* on onion,
*Phakopsara pachyrhizi* and *Phakopsara meibomiae* on soybeans,
*Phomopsis* species on soybeans and sunflowers, *P. viticola* on grapevines,
*Phytophthora infestans* on potatoes and tomatoes,
*Phytophthora* species on various plants, such as, for example, *P. capsici* on bell-peppers,
*Plasmopara viticola* on grapevines,
*Podosphaera leucotricha* on apple,
*Pseudocercosporella herpotrichoides* on cereals,
*Pseudoperonospora* on various plants, such as, for example, *P. cubensis* on cucumber or *P. humili* on hops,
*Pseudopezicula tracheiphilai* on grapevines,
*Puccinia* species on various plants, such as, for example, *P. triticina*, *P. striformins*, *P. hordei* or *P. graminis* on cereals, or *P. asparagi* on asparagus,
*Pyricularia oryzae*, *Corticium sasakii*, *Sarocladium oryzae*, *S. attenuatum*, *Entyloma oryzae* on rice,
*Pyricularia grisea* on lawn and cereals,
*Pythium* spp. on lawn, rice, corn, cotton, oilseed rape, sunflowers, sugar beet, vegetable species and other plants, such as, for example, *P. ultiumum* on various plants, *P. aphanidermatum* on lawn,
*Rhizoctonia* species on cotton, rice, potatoes, lawn, corn, oilseed rape, potatoes, sugar beet, vegetable species and on various plants, such as, for example, *R. solani* on beets and various plants,
*Rhynchosporium secalis* on barley, rye and triticale,
*Sclerotinia* species on oilseed rape and sunflowers,
*Septoria tritici* and *Stagonospora nodorum* on wheat,
*Erysiphe* (syn. *Uncinula*) *necator* on grapevines,
*Setospaeria* species on corn and lawn,
*Sphacelotheca reilinia* on corn,
*Thievaliopsis* species on soybeans and cotton,
*Tilletia* species on cereals,
*Ustilago* species on cereals, corn and sugar cane, such as, for example, *U. maydis* on corn,
*Venturia* species (scab) on apples and pears, such as, for example, *V. inaequalis* on apple.

The co-crystals of pyrimethanil and dithianon are furthermore suitable for controlling harmful fungi in the protection of materials (for example wood, paper, paint dispersions, fibers or fabrics) and in the protection of stored products. In the protection of wood, particular attention is paid to the following harmful fungi: Ascomycetes, such as *Ophiostoma* spp., *Ceratocystis* spp., *Aureobasidium pullulans*, *Sclerophoma* spp., *Chaetomium* spp., *Humicola* spp., *Petriella* spp., *Trichurus* spp.; Basidiomycetes, such as *Coniophora* spp., *Coriolus* spp., *Gloeophyllum* spp., *Lentinus* spp., *Pleurotus* spp., *Poria* spp., *Serpula* spp. and *Tyromyces* spp., Deuteromycetes, such as *Aspergillus* spp., *Cladosporium* spp., *Penicillium* spp., *Trichoderma* spp., *Alternaria* spp., *Paecilomyces* spp. and Zygomycetes, such as *Mucor* spp., additionally in the protection of materials the following yeasts: *Candida* spp. and *Saccharomyces cerevisae*.

In certain circumstances it may be advantageous to add one or more further active compounds to the co-crystals of pyrimethanil and dithianon.

The following list of fungicides, with which the compounds according to the invention can be used in conjunction, is intended to illustrate the possible combinations but does not limit them:

Azoles
triazoles: bitertanol, bromuconazole, cyproconazole, difenoconazole, diniconazole, enilconazole, fenbuconazole, flusilazole, fluquinconazole, flutriafol, hexaconazole, imibenconazole, ipconazole, metconazole, myclobutanil, penconazole, propiconazole, prothioconazole, simeconazole, tebuconazole, tetraconazole, triadimenol, triadimefon, triticonazole;
imidazoles: cyazofamid, imazalil, pefurazoate, prochloraz, triflumizole;
benzimidazoles: benomyl, carbendazim, fuberidazole, thiabendazole;
others: ethaboxam, etridiazole, hymexazole;

Strobilurins
azoxystrobin, dimoxystrobin, enestroburin, fluoxastrobin, kresoxim-methyl, metominostrobin, picoxystrobin, pyraclostrobin, trifloxystrobin, orysastrobin, methyl (2-chloro-5-[1-(3-methylbenzyloxyimino)ethyl]benzyl)carbamate, methyl (2-chloro-5-[1-(6-methylpyridin-2-ylmethoxyimino) ethyl]benzyl)carbamate, methyl 2-(ortho-(2,5-dimethylphenyloxymethylene)phenyl)-3-methoxyacrylate;

Carboxamides
carboxanilides: benalaxyl, benodanil, boscalid, carboxin, mepronil, fenfuram, fenhexamid, flutolanil, furametpyr, metalaxyl, ofurace, oxadixyl, oxycarboxin, penthiopyrad, thifluzamide, tiadinil, N-(4'-bromobiphenyl-2-yl)-4-difluoromethyl-2-methylthiazole-5-carboxamide, N-(4'-trifluoromethylbiphenyl-2-yl)-4-difluoro-methyl-2-methylthiazole-5-carboxamide, N-(4'-chloro-3'-fluorobiphenyl-2-yl)-4-di-fluoromethyl-2-methylthiazole-5-carboxamide, N-(3',4'-dichloro-4-fluorobiphenyl-2-yl)-3-difluoromethyl-1- methylpyrazole-4-carboxamide, N-(2-cyanophenyl)-3,
4-dichloroisothiazole-5-carboxamide;

carboxylic acid morpholides: dimethomorph, flumorph;

benzamides: flumetover, fluopicolide (picobenzamid), zoxamide;

other carboxamides: carpropamid, diclocymet, mandipropamid, N-(2-(4-[3-(4-chloro-phenyl)prop-2-ynyloxy]-3-methoxyphenyl)ethyl)-2-methanesulfonylamino-3-methyl-butyramide, N-(2-(4-[3-(4-chlorophenyl)prop-2-ynyloxy]-3-methoxyphenyl)ethyl)-2-ethanesulfonylamino-3-methylbutyramide;

Nitrogenous Heterocyclyl Compounds pyridines: pyrifenox, 3-[5-(4-chlorophenyl)-2,3-dimethyl-isoxazolidin-3-yl]pyridine;

pyrimidines: bupirimate, ferimzone, fenarimol, mepanipyrim, nuarimol, pyrimethanil;

piperazines: triforine;

pyrroles: fludioxonil, fenpiclonil;

morpholines: aldimorph, dodemorph, fenpropimorph, tridemorph;

dicarboximides: iprodione, procymidone, vinclozolin;

others: acibenzolar-S-methyl, anilazine, captan, captafol, dazomet, diclomezine, fenoxanil, folpet, fenpropidin, famoxadone, fenamidone, octhilinone, probenazole, proquinazid, pyroquilon, quinoxyfen, tricyclazole, 5-chloro-7-(4-methylpiperidin-1-yl)-6-(2,4,6-trifluorophenyl)-[1,2,4]triazolo[1,5-a]pyrimidine, 2-butoxy-6-iodo-3-propyl-chromen-4-one, N,N-dimethyl-3-(3-bromo-6-fluoro-2-methylindole-1-sulfonyl)-[1,2,4]triazole-1-sulfonamide;

Carbamates and Dithiocarbamates dithiocarbamates: ferbam, mancozeb, maneb, metiram, metam, propineb, thiram, zineb, ziram;

carbamates: diethofencarb, flubenthiavalicarb, iprovalicarb, propamocarb, methyl 3-(4-chlorophenyl)-3-(2-isopropoxycarbonylamino-3-methylbutyrylamino)pro-pionate, 4-fluorophenyl N-(1-(1-(4-cyanophenyl)ethanesulfonyl)but-2-yl)carbamate;

Other Fungicides guanidines: dodine, iminoctadine, guazatine;

antibiotics: kasugamycin, polyoxins, streptomycin, validamycin A;

organometallic compounds: fentin salts;

sulfur-containing heterocyclyl compounds: isoprothiolane, dithianon;

organophosphorus compounds: edifenphos, fosetyl, fosetyl-aluminum, iprobenfos, pyrazophos, tolclofos-methyl, phosphorous acid and its salts;

organochlorine compounds: thiophanate-methyl, chlorothalonil, dichlofluanid, tolylfluanid, flusulfamide, phthalide, hexachlorobenzene, pencycuron, quintozene;

nitrophenyl derivatives: binapacryl, dinocap, dinobuton;

inorganic active compounds: Bordeaux mixture, copper acetate, copper hydroxide, copper oxychloride, basic copper sulfate, sulfur;

others: spiroxamine, cyflufenamid, cymoxanil, metrafenone.

The other active components are, if desired, added in a ratio of from 20:1 to 1:20 to the co-crystals of pyrimethanil and dithianon.

Depending on the type of compound and the effect desired, the application rates of the co-crystals according to the invention are from 5 g/ha to 2000 g/ha, preferably from 50 to 900 g/ha, in particular from 50 to 750 g/ha.

The application rates of the co-crystals used in the treatment of seed, for example by dusting, coating or drenching seed, are usually from 1 to 1000 g/100 kg of seed, preferably from 1 to 750 g/100 kg, in particular from 5 to 500 g/100 kg.

When used in the protection of materials or stored products, the amount of co-crystals applied depends on the kind of application area and on the desired effect. Amounts customarily applied in the protection of materials are, for example, 0.001 g to 2 kg, preferably 0.005 g to 1 kg, of active compound per cubic meter of treated material.

The method for controlling harmful fungi is carried out by application of the co-crystals by spraying or dusting the seeds, the plants or the soils before or after sowing of the plants or before or after emergence of the plants.

The figures and examples below serve to illustrate the invention and are not to be understood as limiting it.

FIG. 1: X-ray powder diffractogram of the co-crystals obtained from the formulation of the comparison example on page 16 by drying the formulation overnight on a clay plate FIG. 2: Light microscop picture of a co-crystal of pyrimethanil and dithianon

ANALYSIS

The pictures of the X-ray powder diffractograms were taken using a D-5000 diffractometer from Siemens in reflection geometry in the range from $2\theta=4°-35°$ with increments of $0.02°$ using Cu—Kα radiation at 25° C. The 2θ values found were used to calculate the stated interplanar spacing d.

The crystallographic data of modifications II and IV (Tables 1 and 2) were determined on a single-crystal diffractometer from Siemens using Cu—Kα radiation.

Melting point measurement was done with a Mettler Toledo Hot Stage microscope with a heating rate of 5° C./minute.

The particle sizes in the suspension concentrates were determined using a Mastersizer 2000 from Malvern Instruments GmbH.

COMPARISON EXAMPLE

A mixture of 65 g urea, 43 g of Reax 910, 2 g Lutensit A-BO, 20 g Morwet 3D 425, 2 g Acticide MBS and 250 g deionised water is homogenized under stirring until a clear solution is obtained. 305.21 g pyrimethanil technical grade active ingredient (TGAI) and 318.1 dithianon TGAI are added to this solution. The resulting suspension is milled over a glass-bead mill to obtain a particle size distribution of 80%<2 μm. During the milling the temperature rises to approx. 35° C. and the colour of the suspension has turned from brown to dark green. The necessary amount of demineralized water is added to give the required concentration of active ingredients. The viscosity is at this point below 100 mPas. One day after preparation, the suspension has the consistency if thick paste. Several days later, the suspension has completely solidified and cannot be poured out of the container anymore.

EXAMPLE 1

Two separate premixes are prepared

Premix A:

A mixture of 35 g 1,2-Propylenglykol, 10 g of Soprophor BSU, 15 g Pluronic PE 10500, 5 g Atplus 245, 1 g of Acticide MBS and 125 g deionised water is homogenized under stirring until a clear solution is obtained. 300 g Pyrimethanil are added to this solution. The resulting suspension is milled over a glass-bead mill to obtain a particle size distribution of 80%<2 μm.

Premix B:

A mixture of 35 g 1,2-Propylenglykol, 10 g of Soprophor BSU, 15 g Pluronic PE 10500, 5 g Atplus 245, 1 g of Acticide MBS and 125 g deionised water is homogenized under stirring until a clear solution is obtained. 300 g Dithianon are added to this solution. The resulting suspension is milled over a glass-bead mill to obtain a particle size distribution of 80%<2 µm.

The two premixes A and B are mixed together in one beaker under stirring at 50° C. After one hour, the suspension has changed from brown colored to dark green. The suspension is cooled to 20° C. and then milled over a glass-bead mill to obtain a particle size distribution (PSD) 80%<2 µm. The product has a viscosity of less than 50 mPas.

The product stays unchanged at room temperature for at least 4 months. The particle size distribution is very stable during this time.

EXAMPLE 2

The premixes A and B are passed continuously over a bead-mill at elevated temperature. After half an hour, the complete suspension has turned dark green. The mill is cooled to 20° C. and milling is extended until a PSD of 80%<2 µm is achieved.

EXAMPLE 3

A mixture of 70 g 1,2-Propylenglykol, 20 g of Soprophor BSU, 30 g Pluronic PE 10500, 10 g Atplus 245, 2 g of Acticide MBS and 250 g deionised water is homogenized under stirring until a clear solution is obtained. 300 g Pyrimethanil is added to this solution. The resulting suspension is milled over a glass-bead mill to obtain a particle size distribution of 80%<2 µm. To this suspension premix is added 300 g dithianon under agitation. After all dithianon has been added, the mixture is heated to 50° C. for 1 hour. The suspension has turned dark green and after cooling it down to 20° C. it is being milled over a bead mill to obtain a PSD of 80%<2 µm.

EXAMPLE 4

A mixture of 70 g 1,2-Propylenglykol, 20 g of Soprophor BSU, 30 g Pluronic PE 10500, 10 g Atplus 245, 2 g of Acticide MBS and 250 g deionised water is homogenized under stirring until a clear solution is obtained. 300 g Dithianon is added to this solution. The resulting suspension is milled over a glass-bead mill to obtain a particle size distribution of 80%<2 µm. To this suspension premix is added 300 g pyrimethanil under agitation. After all pyrimethanil has been added, the mixture is heated to 50° C. for 1 hour. The suspension has turned dark green and after cooling it down to 20° C. it is being milled over a bead mill to obtain a PSD of 80%<2 µm

EXAMPLE 5

Dithianon and pyrimethanil are suspended together with suitable dispersants and emulsifiers in a mineral or vegetable based oil (like white oil, Bayol 85, sun flower oil, rape seed oil, corn oil, also methyloleate). The OD (oil dispersion) premix is heated under stirring to 50° C. until the colour of the suspension has turned from brown to dark green (1 hour). Then the premix is cooled down and grinded over a bead mill to obtain a PSD of 80%<2 µm.

EXAMPLE 6

Solutions of 296.3 g dithianon and 199.4 pyrimethanil in polar sovnets like DMSO, Acetonitril, DMF or aceton are prepared. The solutions are mixed and the solvent is evaporated to yield 495.6 g of the co-crystals. These are suspended in water+formulation additives (same as for suspension concentrate) and first pre-ground over a PUC mill and then finely ground over a bead mill to achieve a PSD of 80%<2 µm.

EXAMPLE 7

Dry dithianon and pyrimethanil are thoroughly mixed and kept at 50° C. under agitation. After a couple of hours, the powdery product has turned its colour to olive green. To the cooled co-crystal premix, dispersants, antifoams, wetting agents, adjuvants and fillers are added as typical for WG, WP and WDG formulations. Then the premix is processed either by extrusion to give a WDG (water dispersible granule) formulation or it is used after a finishing step as WP (wettable powder). It may also be suspended in water and then spray dried to give a water dispersible granule.

EXAMPLE 8

A suspension premix of pyrimethanil and dithianon is being prepared as described in example no. 3. This premix is then run over a bead mill to give a PSD of 80%<2 µm. The resulting suspension is then spray dried to give a WDG formulation.

The invention claimed is:

1. Co-crystals of pyrimethanil and dithianon, which, in a X-ray powder diffractogram at 25° C., show at least three of the following reflexes:
   $2\theta=7.46\pm0.20$
   $2\theta=9.98\pm0.20$
   $2\theta=13.28\pm0.20$
   $2\theta=23.09\pm0.20$
   $2\theta=24.38\pm0.20$
   $2\theta=27.01\pm0.20$.

2. Co-crystals according to claim 1 having a melting point in the range of 165 to 175°.

3. A process for the preparation of the co-crystals according to claim 1, comprising the following steps:
   i) dissolving equimolar amounts of pyrimethanil and dithianon in a polar organic solvent,
   ii) evaporating the solvent to form the co-crystals.

4. A process for the preparation of the co-crystals according to claim 1, comprising the following steps:
   i) dry-mixing equimolar amounts of pyrimethanil and dithanion to form a premix,
   ii) dry-grinding the premix to form the co-crystals.

5. A process for the preparation of the co-crystals according to claim 1, comprising the following steps:
   i) mixing equimolar amounts of pyrimethanil and dithianon with a liquid carrier to form a premix,
   ii) grinding the premix to form the co-crystals on the carrier,
   iii) separating the co-crystals from the carrier.

6. A composition for crop protection, comprising co-crystals according to claim 1 and carriers and/or auxiliaries.

7. The composition of claim 6 in the form of an aqueous based suspension concentrate.

8. The composition of claim 6 in the form of an aqueous or vegetable or mineral oil based suspension concentrate.

9. A process for the preparation of an aqueous suspension concentrate, comprising the following steps:
   i) adding pyrimethanil into water which contains one or more dispersing agents and optionally other auxiliaries to form a premix A, ii) adding dithianon into water which contains one or more dispersing agents and optionally other auxiliaries to form a premix B, iii) mixing the premixes A and B together under stirring at a temperature from 20° C. to 150° C. to form a dark green suspension of co-crystals according claim 1, iv) milling the so obtained suspension to a particle size distribution 80%<2 μm.

10. A process for the preparation of an aqueous suspension concentrate, comprising the following steps:

i) adding pyrimethanil into water which contains one or more dispersing agents and optionally other auxiliaries to form a premix A, ii) mixing the premix A with dithianon under stirring at a temperature from 20° C. to 150° C. to form a dark green suspension of co-crystals according claim 1, iii) milling the so obtained suspension to a particle size distribution 80%<2 μm.

11. A process for the preparation of an aqueous suspension concentrate, comprising the following steps:

i) adding dithianon into water which contains one or more dispersing agents and optionally other auxiliaries to form a premix B, ii) mixing the premix B with pyrimethanil under stirring at a temperature from 20° C. to 150° C. to form a dark green suspension of co-crystals according claim 1, iii) milling the so obtained suspension to a particle size distribution 80%<2 μm.

12. The process according to claim 9, wherein the temperature in step iii) is from 40 to 60° C.

13. The process according to claim 9, wherein the temperature in step iv) is from 20 to 30° C.

14. An aqueous suspension concentrate, comprising co-crystals of pyrimethanil and dithianon according to claim 1, water and auxiliaries.

15. A method for controlling phytopathogenic fungi comprising spraying or dusting the seeds, the plants or the soils before or after sowing of the plants or before or after emergence of the plants with a composition comprising co-crystals of claim 1.

16. The method of claim 15, wherein the co-crystals have a melting point in the range of 165 to 175°.

17. The method of claim 15, wherein the co-crystals were prepared by i) adding pyrimethanil into water which contains one or more dispersing agents and optionally other auxiliaries to form a premix A, ii) adding dithianon into water which contains one or more dispersing agents and optionally other auxiliaries to form a premix B, iii) mixing the premixes A and B together under stirring at a temperature from 20° C. to 150° C. to form a dark green suspension of co-crystals according claim 1, iv) milling the so obtained suspension to a particle size distribution 80%<2 μm.

18. The method of claim 15, wherein the co-crystals were prepared by i) adding pyrimethanil into water which contains one or more dispersing agents and optionally other auxiliaries to form a premix A, ii) mixing the premix A with dithianon under stirring at a temperature from 20° C. to 150° C. to form a dark green suspension of co-crystals according claim 1, iii) milling the so obtained suspension to a particle size distribution 80%<2 μm.

19. The method of claim 15, wherein the co-crystals were prepared by i) adding dithianon into water which contains one or more dispersing agents and optionally other auxiliaries to form a premix B, ii) mixing the premix B with pyrimethanil under stirring at a temperature from 20° C. to 150° C. to form a dark green suspension of co-crystals according claim 1, iii) milling the so obtained suspension to a particle size distribution 80%<2 μm.

20. The method of claim 17, wherein the temperature in step iii) is from 40 to 60° C.

* * * * *